(12) United States Patent
Charbonneau et al.

(10) Patent No.: US 7,985,738 B2
(45) Date of Patent: Jul. 26, 2011

(54) CYTOSINE NUCLEOSIDE ANALOGS AND ISOFLAVONES AND USES THEREOF

(75) Inventors: Michel Charbonneau, Laval (CA); Noel Jean-Marie Raynal, Montreal (CA); Richard Lewis Momparler, Outremont (CA); Louise F. Momparler, Outremont (CA)

(73) Assignee: Institut National de la Recherche Scientifique, Quebec (CA)

( * ) Notice: Subject to any disclaimer, the term of this patent is extended or adjusted under 35 U.S.C. 154(b) by 346 days.

(21) Appl. No.: 12/126,493

(22) Filed: May 23, 2008

(65) Prior Publication Data

US 2008/0293651 A1 Nov. 27, 2008

Related U.S. Application Data

(60) Provisional application No. 60/939,752, filed on May 23, 2007.

(30) Foreign Application Priority Data

May 23, 2007 (CA) ..................................... 2590048

(51) Int. Cl.
*A61K 31/70* (2006.01)
*A61K 31/35* (2006.01)
*C07H 19/12* (2006.01)
*C07D 311/00* (2006.01)
(52) U.S. Cl. .......... 514/43; 514/456; 536/28.3; 549/403
(58) Field of Classification Search ........................ None
See application file for complete search history.

(56) References Cited

U.S. PATENT DOCUMENTS

| 5,637,703 | A | 6/1997 | Mazurek et al. |
| 6,613,753 | B2 | 9/2003 | Rubinfeld et al. |
| 6,982,253 | B2 | 1/2006 | Joshi-Hangal et al. |
| 7,135,464 | B2 | 11/2006 | Joshi-Hangal et al. |

FOREIGN PATENT DOCUMENTS

WO 00/03707 1/2000

OTHER PUBLICATIONS (R) Li et al., "Genistein Depletes Telomerase Activity Through Cross-talk Between Genetic and Epigenetic Mechanisms," International Journal of Cancer, 125(2), 286-296 (2009).*
(S) Fang et al., "Reversal of Hypermethylation and Reactivation of p16INK4a , RARβ, and MGMT Genes by Genistein and Other Isoflavones from Soy," Clinical Cancer Research, 11(19), 7033-7041 (Oct. 1, 2005).*
Raynal, N. J.-M. et al. Genistein, a Soy Isoflavone, Can Enhance the Antineoplastic Action of 5-AZA-2'Deoxycytidine on Leukemic Cells. The 11th International Conference on Differentiation Therapy, Nov. 4-8, 2006, France.
Raynal, N. J.-M. et al. La genisteine: une isoflavone du soja comme facteur de chemoprevention en sante environnementale. Journee de recherche, May 24, 2006. Montreal, Canada.
Shen, J. et al. Synergistic Antileukemia Effect of Genistein and Chemotherapy in Mouse Xenograft Model and potential mechanism through MAPK signaling. Exp Hematology, 2007, 35:pp. 75-83.
Issa et al., Phase 1 study of low-dose prolonged exposure schedules of the hypomethylating agent 5-aza-2'-deoxycytidine (decitabine) in hematopoietic malignancies, Blood, vol. 103, No. 5, pp. 1635-1640 (2004).
Raynal et al., Synergistic Effect of 5-Aza-2'-Deoxycytidine and Genistein in Combination Against Leukemia, Oncology Research, vol. 17, pp. 223-230 (2008).
Roper et al., Comparison of In Vitro Methods to Determine Drug-induced Cell Lethality, Cancer Research, vol. 36, pp. 2182-2188 (1976).

* cited by examiner

*Primary Examiner* — Lawrence E Crane
(74) *Attorney, Agent, or Firm* — Fish & Richardson P.C.

(57) ABSTRACT

Methods, uses, compositions and kits relating to the inhibition and/or prevention of undesirable cell proliferation, and prevention and/or treatment of diseases or disorders associated with such proliferation, such as cancer, using a cytosine nucleoside analog such as 5-aza-2'-deoxycytidine and an isoflavone such as genistein, are described.

10 Claims, 8 Drawing Sheets

CYTOSINE NUCLEOSIDE ANALOGS AND ISOFLAVONES AND USES THEREOF

CROSS REFERENCE TO RELATED APPLICATIONS

This application claims the benefit, under 35 U.S.C. §119 (e), of U.S. provisional application Ser. No. 60/939,752 filed on May 23, 2007. This application also claims the benefit, under 35 U.S.C. §119(a), of Canadian application No. 2,590,048 filed on May 23, 2007. Both of these applications are incorporated herein by reference in their entirety.

FIELD OF THE INVENTION

The present invention relates to the use of cytosine nucleoside analogs and isoflavones and more particularly relates to their use for inhibiting undesirable proliferation of cells.

BACKGROUND OF THE INVENTION

Chemotherapy constitutes one of the major therapeutic approaches for the treatment of cancer, along with surgery and radiotherapy. However, the usefulness of commonly used anti-cancer drugs is severely limited by their toxicity towards normal tissues, particularly the rapidly proliferating cells of the gastrointestinal tract and bone marrow. In addition, these drugs are affected by the mechanisms of multi-drug resistance.

Nucleoside analogs have been studied for their antitumor effects. For example, the cytosine nucleoside analogs 5-azacytidine (azacitidine), 5-aza-2'-deoxycytidine (decitabine), 1-β-D-arabinofuranosyl-5-azacytosine (fazarabine), 1-β-D-arabinofuranosylcytosine (cytosine arabinoside, cytarabine, Ara-C) and dihydro-5-azacytidine (DHAC) have been used clinically in cancer treatment.

There is evidence, however, that such agents may be harmful and/or ineffective in some settings. Moreover, both azacytidine and decitabine have the common side effect of inducing nausea, vomiting, diarrhea and myelosuppression that limit doses and duration of treatment (Christman J K, (2002). *Oncogene* 21(35): 5483-5495).

As such, there is a continued need to develop new treatments for cancer.

The present description refers to a number of documents, the content of which is herein incorporated by reference in their entirety.

SUMMARY OF THE INVENTION

The present invention relates to the use of a cytosine nucleoside analog and an isoflavone for the inhibition of undesirable cell proliferation (e.g., tumor/cancer cell proliferation), and/or for prevention/treatment of associated disease such as cancer.

Therefore, in a first aspect, the present invention provides a method of inhibiting undesirable cell proliferation (e.g., tumor/cancer cell proliferation) in a subject, the method comprising administering 5-aza-2'-deoxycytidine and an isoflavone to the subject.

In another aspect, the present invention provides a method of inhibiting undesirable cell proliferation (e.g., tumor/cancer cell proliferation) in a biological system, the method comprising contacting the system with 5-aza-2'-deoxycytidine and an isoflavone.

In another aspect, the present invention provides a kit or package comprising 5-aza-2'-deoxycytidine together with instructions for its use in combination with an isoflavone for inhibiting undesirable cell proliferation (e.g., tumor/cancer cell proliferation) and/or preventing or treating cancer.

In a further aspect, the present invention provides a kit or package comprising an isoflavone together with instructions for its use in combination with 5-aza-2'-deoxycytidine for inhibiting undesirable cell proliferation (e.g., tumor/cancer cell proliferation) and/or for preventing or treating cancer.

In another aspect, the present invention provides a kit or package comprising 5-aza-2'-deoxycytidine and an isoflavone together with instructions for inhibiting undesirable cell proliferation (e.g., tumor/cancer cell proliferation) and/or for preventing or treating cancer.

In a further aspect, the present invention provides a composition for inhibiting undesirable cell proliferation (e.g., tumor/cancer cell proliferation) and/or for preventing or treating cancer, said composition comprising 5-aza-2'-deoxycytidine and an isoflavone.

In another aspect, the present invention provides the use of 5-aza-2'-deoxycytidine and an isoflavone for the preparation of a medicament.

In another aspect, the present invention provides the use of 5-aza-2'-deoxycytidine and an isoflavone for inhibiting undesirable cell proliferation (e.g., tumor/cancer cell proliferation) and/or for preventing or treating cancer.

In a further aspect, the present invention provides the use of 5-aza-2'-deoxycytidine and an isoflavone for the preparation of a medicament for inhibiting undesirable cell proliferation (e.g., tumor/cancer cell proliferation) and/or for preventing or treating cancer.

In another embodiment, the above-mentioned isoflavone is genistein.

In an embodiment, the above-mentioned method is for the prevention or treatment of cancer. In a further embodiment, the above-mentioned cancer is leukemia, lung cancer, breast cancer or colon cancer. In yet a further embodiment, the above-mentioned leukemia is myeloid leukemia or lymphoid leukemia.

In an embodiment, the above-mentioned cells are resistant to treatment with an antitumor agent (e.g., a cytosine nucleoside analog) in the absence of said isoflavone. In a further embodiment, the above-mentioned cells are resistant to treatment with cytosine arabinoside or 5-aza-2'-deoxycytidine.

In an embodiment, the above-mentioned subject is a mammal. In a further embodiment, the above-mentioned mammal is a human.

In an embodiment, the above-mentioned 5-aza-2'-deoxycytidine and isoflavone are administered or used simultaneously.

In another embodiment, the above-mentioned 5-aza-2'-deoxycytidine and isoflavone are administered or used sequentially.

In an embodiment, the above-mentioned method comprises administering a composition comprising the above-mentioned 5-aza-2'-deoxycytidine and isoflavone.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1A:
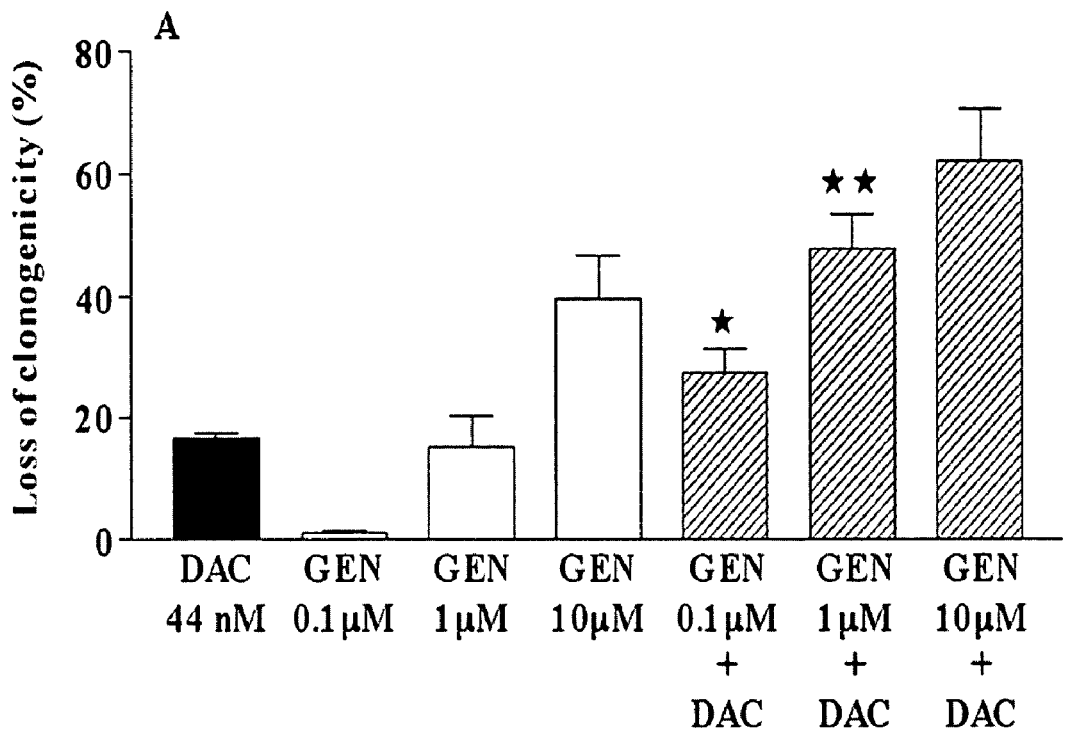
FIG. 1 shows the synergistic activation of 5-aza-2'-deoxycytidine (decitabine; DAC) on loss of clonogenicity in human leukemic cell lines. Results of loss of clonogenicity are expressed as mean±standard error of the mean (SEM) compared to control cells (n=3). (A) HL-60 myeloid and (B) MOLT-3 lymphoid human leukemic cell lines were exposed 48 h with DAC (44 nM) alone or in combination with different concentrations of genistein (0.1, 1 and 10 µM). *:p<0.05, **:p<0.01.

The present inventors have determined that the combination of an isoflavone with a cytosine nucleoside analog (5-aza-2'-deoxycytidine) is effective at reducing or inhibiting the growth of tumor cells in vitro and in vivo.

In an aspect, the present invention provides a method for inhibiting undesirable or uncontrolled cell proliferation or treating a disease associated with undesirable or uncontrolled cell proliferation in a subject comprising administrating an effective amount of 5-aza-2'-deoxycytidine and an isoflavone, or prodrugs, analogs, derivatives or salts thereof, to said subject.

In another aspect, the present invention provides a method for inhibiting undesirable or uncontrolled cell proliferation (e.g., of a tumor or cancer cell) comprising contacting (e.g., in vitro) said cell with 5-aza-2'-deoxycytidine and an isoflavone, or prodrugs, analogs, derivatives or salts thereof.

In another aspect, the present invention provides a combination for inhibiting undesirable or uncontrolled cell proliferation or for the treatment of a disease associated with undesirable or uncontrolled cell proliferation in a subject, the combination comprising 5-aza-2'-deoxycytidine and an isoflavone, or prodrugs, analogs, derivatives or salts thereof.

In another aspect, the present invention provides a composition for inhibiting undesirable or uncontrolled cell proliferation (e.g., of a tumor cell) or for the prevention or treatment of a disease associated with undesirable or uncontrolled cell proliferation in a subject, the composition comprising 5-aza-2'-deoxycytidine and an isoflavone, or prodrugs, analogs, derivatives or salts thereof.

In another aspect, the present invention provides a use of 5-aza-2'-deoxycytidine and an isoflavone, or prodrugs, analogs, derivatives or salts thereof, for inhibiting undesirable or uncontrolled cell proliferation (e.g., of a tumor or cancer cell) or for the prevention or treatment of disease associated with undesirable or uncontrolled cell proliferation.

The present invention further provides the use of 5-aza-2'-deoxycytidine and an isoflavone, or prodrugs, analogs, derivatives or salts thereof, for the manufacture of a medicament or for providing new dosage regimen for an existing medicament, e.g., for inhibiting undesirable or uncontrolled cell proliferation (e.g., of a tumor or cancer cell) or for the prevention and/or treatment of disease associated with undesirable or uncontrolled cell proliferation.

Isoflavones useful in the method, uses, kits and compositions of the present invention may be obtained and isolated from the plant materials in which they naturally occur. The isoflavone compound may be extracted from a plant (e.g., soybeans) using methods well-known in the art. For example, the plant materials may be extracted with an alcohol (e.g., methanol, ethanol), or an aqueous solution (e.g., an aqueous alkaline solution), to remove the isoflavones from the plant material. The isoflavone compounds may be isolated from the extract by conventional separation procedures such as reverse phase high performance liquid chromatography ("HPLC").

Isoflavones can also be synthetically prepared by processes known in the art. For example, genistein can be synthetically prepared by the methods provided by Baker and Robinson (*J. Chem. Soc.*, p. 3115 (1928)); Narasimhachari et. al. (*J. Sci. Ind. Res.*, 12: 287 (1953)); Yoder et al., (*Proc. Iowa Acad. Sci.*, 61: 271 (1954)); and Zemplen et al. (*Acta. Chim. Acad. Sci. Hung.*, 19: 277 (1959)), each reference of which is incorporated herein by reference. Examples of isoflavones include genistein, daidzein, glycitein, biochanin A, and formononetin. These isoflavones can be represented by the following general formula (I):

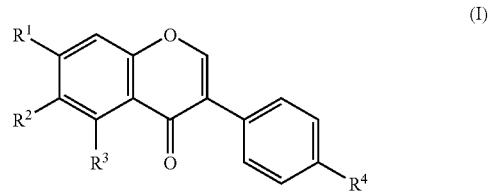

(I)

Genistein: $R^1$ = OH, $R^2$ = H, $R^3$ = OH and $R^4$ = OH
Daidzein: $R^1$ = OH, $R^2$ = H, $R^3$ = H and $R^4$ = OH
Glycitein: $R^1$ = OH, $R^2$ = OCH$_3$, $R^3$ = H and $R^4$ = OH
Biochanin A: $R^1$ = OH, $R^2$ = H, $R^3$ = OH and $R^4$ = OCH$_3$
Formononetin: $R^1$ = OH, $R^2$ = H, $R^3$ = H and $R^4$ = OCH$_3$ Glucosides of isoflavones may also be naturally found in plants or synthesized. Glucosides of genistein (genistin), daidzein (daidzin) and glycitein (glycitin) can be represented by the following general formula (II):

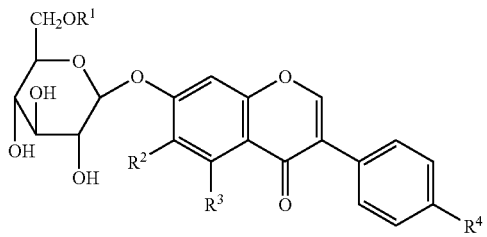

(II)

Genistin: $R^1 = H, R^2 = H, R^3 = OH$ and $R^4 = OH$
6'-OMal genistin: $R^1 = COCH_2CO_2H, R^2 = H, R^3 = OH$ and $R^4 = OH$
6'-OAc genistin: $R^1 = COCH_3, R^2 = H, R^3 = OH$ and $R^4 = OH$
Daidzin: $R^1 = H, R^2 = H, R^3 = H$ and $R^4 = OH$
6'-OMal daidzin: $R^1 = COCH_2CO_2H, R^2 = H, R^3 = H$ and $R^4 = OH$
6'-OAc daidzin: $R^1 = COCH_3, R^2 = H, R^3 = H$ and $R^4 = OH$
Glycitin: $R^1 = H, R^2 = OCH_3, R^3 = H$ and $R^4 = OH$
6'-OMal glycitin: $R^1 = COCH_3, R^2 = OCH_3, R^3 = H$ and $R^4 = OH$ Glucosides of isoflavones may be converted to their respective aglycone isoflavone forms using methods well known in the art (see, e.g., EP 1 159 963 A1). The conversion of the isoflavone glucoside conjugates and the isoflavone glucosides to the aglycone isoflavones can be effected in the substrate from which the isoflavones are to be extracted prior to the extraction, or may be effected in the isoflavone enriched extract after separation of the extract from the insoluble materials.

Several isoflavones are commercially available. For example, genistein may be purchased from LC Laboratories (Woburn, Mass.) and synthetic genistein (Bonistein™) may be purchased from DSM Nutritional Products (Basel, Switzerland).

In an embodiment, the above-mentioned isoflavone is genistein, daidzein, glycitein, biochanin A, or formononetin. In yet a further embodiment, the above-mentioned isoflavone is genistein.

5-aza-2'-deoxycytidine (4-Amino-1-(2-deoxy-β-D-ribofuranosyl)-1,3,5-triazin-2(1H)-one; CAS number 2353-33-5), also called ZdCyd, 5-azadeoxycytidine, 2-desoxy-5-azacytidine, 5-azadCyd, 5-azadCdr, Decitabine and Dacogen™, is a chemical analog of the cytosine nucleoside. It has the following formula (III):

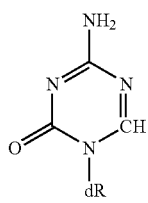

(III)

dR = desoxyribose

The term "prodrug" as used herein is defined as a compound that is administered in an inactive or significantly less active form and which is metabolized in vivo (e.g., after administration to a subject) into an active or more active metabolite. The term "analog" as used herein is defined as a compound with a structure similar to the "original" compound, but with some differences as compared to the original, and which still maintain one or more(s) of the biological properties of the original compound. The term "derivative" as used herein is defined as a chemical compound that may be synthesized or reacted from another compound of similar structure in one or more steps. Examples of this are the addition of a hydrogen group by an alkyl, aryl, acyl, or amino group to the nucleus of the molecule. Biologically active derivatives also share the effector function of the native molecule on tumor cells. The prodrug, analog or derivative may, for example, have a better bioavailability or enhanced solubility in water. "Salts" (pharmaceutically acceptable salts) include salts of the active compounds described herein (e.g., 5-aza-2'-deoxycytidine, isoflavone) which are prepared with relatively nontoxic acids or bases, depending on the particular substituents found on the compounds described herein.

Isoflavone analogs or derivatives are well known in the art (see, for example, published US Patent applications No. 2006/0251592, No. 2006/0106220, and No. 2005/0096381). The analogs and derivatives may be, for example, pharmaceutically acceptable salts and esters.

"Treatment" or "treating" a disease (e.g., a proliferative disease; cancer) as used herein refers to the administration of one or more compound(s) to elicit a desired therapeutic medicinal/biological response in a tissue, system, animal, individual or human, in order to have one or more of the following effects:

(A) Inhibiting the disease; for example, inhibiting a disease, condition or disorder associated with undesirable or uncontrolled cell proliferation (e.g., by inhibiting the replication of abnormal/hyperproliferative cells and/or reducing the number of abnormal cells in the body and/or reducing the spread of abnormal cells within the body) in an individual that is experiencing or displaying the pathology or symptomatology of the disease, condition or disorder (i.e., arresting further development of the pathology and/or symptomatology); and (B) Ameliorating the disease; for example, ameliorating disease, condition or disorder associated with undesirable or uncontrolled cell proliferation in an individual that is experiencing or displaying the pathology or symptomatology of the disease, condition or disorder (i.e., reversing the pathology and/or symptomatology).

"Prevention" or "preventing" a disease as used herein refers to the administration of one or more compound(s) to elicit a desired prophylactic medicinal/biological response in a tissue, system, animal, individual or human. For example, preventing a disease, condition or disorder associated with undesirable or uncontrolled cell proliferation (e.g., by inhibiting/blocking the transformation of a normal cell into an abnormal, hyperproliferative cell) in an individual that may not yet experience or display the pathology or symptomatology of the disease.

The present invention relates to the administration of 5-aza-2'-deoxycytidine and an isoflavone, to elicit any of the effects discussed above. 5-aza-2'-deoxycytidine and an isoflavone may be administered alone or in combination with at least one other agent, such as stabilizing compound, which may be administered in any sterile, biocompatible pharmaceutical carrier, including, but not limited to, saline, buffered saline, dextrose, and water. 5-aza-2'-deoxycytidine and an isoflavone may be administered alone or in combination with other agents, drugs or hormones. 5-aza-2'-deoxycytidine and an isoflavone utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means. The cytosine nucleoside analog and the isoflavone may be administered separately or in combination (e.g., together in a composition). The combination of therapeutic agents and compositions of the present invention may be administered or co-administered in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, the isoflavone may be administered to a patient before, concomitantly, before and after, or after 5-aza-2'-deoxycytidine is administered.

As such, the invention further provides a composition comprising 5-aza-2'-deoxycytidine and a pharmaceutically acceptable diluent or carrier; a composition comprising an isoflavone and a pharmaceutically acceptable diluent or carrier; a composition comprising 5-aza-2'-deoxycytidine and an isoflavone; and a composition comprising 5-aza-2'-deoxycytidine, an isoflavone and a pharmaceutically acceptable diluent or carrier.

In addition to the active ingredients (e.g., 5-aza-2'-deoxycytidine, an isoflavone, or both), pharmaceutical compositions may contain suitable pharmaceutically-acceptable carriers comprising excipients and auxiliaries, which facilitate processing of the active compounds into preparations, which can be used pharmaceutically. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders (see Remington: The Science and Practice of Pharmacy by Alfonso R. Gennaro, 2003, 21$^{th}$ edition, Mack Publishing Company).

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick sustained or delayed release of the active ingredient after administration to the patient by employing procedures known in the art.

Pharmaceutical compositions suitable for use in the invention include compositions wherein the active ingredients are contained in an effective amount to achieve the intended purpose (e.g., preventing and/or ameliorating and/or inhibiting a disease). The determination of an effective dose is well within the capability of those skilled in the art. For any compounds, the therapeutically effective dose can be estimated initially either in cell culture assays, e.g., tumor cell lines or in animal models, usually mice, rabbits, dogs or pigs. The animal model may also be used to determine the appropriate concentration range and route of administration. Such information can then be used to determine useful doses and routes for administration in humans. An effective dose or amount refers to that amount of one or more active ingredient(s), for example an isoflavone and 5-aza-2'-deoxycytidine, which is sufficient for treating a specific disease or condition (e.g., a disease associated with undesirable or uncontrolled cell proliferation). Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Guidance as to particular dosages and methods of delivery is provided in the literature and generally available to practitioners in the art.

5-aza-2'-deoxycytidine may be administered to a patient by injection (e.g., bolus intravenous (i.v.) injection, continuous i.v. infusion and i.v. infusion). For example, 5-aza-2'-deoxycytidine may be administered into the patient via a 1-24 hour i.v. infusion per day, for about 1-5 days per treatment cycle, at a dose ranging from about 1 to about 1000 mg/m$^2$/day. 5-aza-2'-deoxycytidine may be supplied as a sterile lyophilized powder for injection, together with buffering salt, such as potassium dihydrogen phosphate, and pH modifier, such as sodium hydroxide. 5-aza-2'-deoxycytidine may be prepared and formulated as described in U.S. Pat. No. 6,982,253.

The isoflavone may be administered orally to a patient about 1 to about 15 days before the cytosine nucleoside analog infusion and throughout the recovery period for a maximum of about 5 weeks after the infusion, at a dose that produces plasma levels of total isoflavones about 0.1 to about 50 micromolar (μM).

In an embodiment, the above-mentioned composition further comprises one or more additional active agent(s) (e.g., an anti-cancer/anti-neoplastic agent).

In an embodiment, the above-mentioned disease associated with undesirable or uncontrolled cell proliferation is a benign tumor (e.g., hemangiomas, acoustic neuromas, neurofibroma, trachomas and pyogenic granulomas), a cancer (including primary tumors and tumor metastasis), or an abnormal stimulation of endothelial cells (e.g., atherosclerosis).

In an embodiment, the above-mentioned disease associated with undesirable or uncontrolled cell proliferation is cancer. In a further embodiment, the above-mentioned cancer is breast cancer, colon cancer, lung cancer or a cancer of the blood or lymphatic system (e.g., Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoletic and related tissues, for example diffuse large cell lymphoma, T-cell lymphoma or cutaneous T-cell lymphoma).

In an embodiment, the above-mentioned cancer or cell is resistant to treatment with an antitumor agent alone (i.e. in the absence of the isoflavone). In an embodiment, the above-mentioned antitumor agent is a cytosine nucleoside analog (e.g., 5-aza-2'-deoxycytidine).

As used herein, a synergistic effect (e.g., reduction in cancer cell number, clonogenicity, or increase in survival time) is achieved when the effect of the combined drugs is greater than the theoretical sum of the effect of each agent alone. One potential advantage of combination therapy with a synergistic effect is that lower dosages of one or both of the drugs or therapies may be used in order to achieve high therapeutic activity with low toxicity (e.g., a lower dose of 5-aza-2'-deoxycytidine and an isoflavone provides anti-cancer activity with lower toxicity). In an embodiment, the combination therapy results in at least a 5% increase in the effect as compared to the predicted theoretical additive effect of the agents. In a further embodiment, the combination therapy results in at least a 10% increase in the effect as compared to the predicted theoretical additive effect of the agents. In a further embodiment, the combination therapy results in at least a 20% increase in the effect as compared to the predicted theoretical additive effect of the agents. In a further embodiment, the combination therapy results in at least a 30% increase in the effect as compared to the predicted theoretical additive effect of the agents. In a further embodiment, the combination therapy results in at least a 50% increase in the effect as compared to the predicted theoretical additive effect of the agents.

The present invention further provides a kit comprising an agent, combination of agents or composition(s) of the present invention. The arrangement and construction of such kits is conventionally known to one of skill in the art. Such kits may include, for example, container(s) (e.g. syringe and/or vial and/or ampoule) for containing the agent or combination of agents or compositions, other apparatus for administering the therapeutic agent(s) and/or composition(s) and/or diluent(s). The kit may optionally further include instructions. The instructions may describe how the agent(s) and the diluent should be mixed to form a pharmaceutical formulation. The instructions may also describe how to administer the resulting pharmaceutical formulation to a subject.

In an embodiment, the above-mentioned kit comprises instructions for the treatment of a disease associated with undesirable or uncontrolled cell proliferation (e.g., cancer) in a subject.

As used herein, the terms "subject" or "patient" are used interchangeably are used to mean any animal, such as a mammal, including humans and non-human primates. In an embodiment, the above-mentioned subject is a mammal. In a further embodiment, the above-mentioned subject is a human.

The present invention is illustrated in further details by the following non-limiting examples.

EXAMPLES

Example 1

Material and Methods

Cell lines and drug exposure. Human myeloid (HL-60) and lymphoid (MOLT-3) leukemic cells were obtained from ATCC (ATCC #: CRL-1552; Manassas, Va. USA). MBA-MD-231 and Dld-1 cells were also used. Human cell lines were cultured in RPMI-1640 medium (Invitrogen, Burlington, Ontario) supplemented with 10% heat-inactivated fetal bovine serum (Wisent, St-Bruno, Quebec). The doubling times of HL-60 and MOLT-3 were 16-18 h and 23-24 h, respectively, whereas for both MBA-MD-231 and Dld-1 cells it was 24-27 h. The murine lymphoid leukemic cell line L1210 (ATCC #: CCL-219; Brandes et al., (1966). *J Natl Cancer Inst.* 37(4): 467-85) was cultured in RPMI-1640 with 5% heat-inactivated fetal calf serum and with 6 µM of 2-mercaptoethanol. The doubling time of the L1210 cells was about 10 h. From this cell line, a clone fully resistant to decitabine, identified herein as L1210/ARAC, was generated after exposure of increasing doses of cytosine arabinoside for a period of 3 months (Schabel et al., (1984). *Cancer Treat. Rep* 67: 905-922). The doubling time of the L1210/ARAC cells was about 12 h. Human lung adenocarcinoma cells H2087, and Calu-6 non-small cell lung cancer cells, were obtained from ATCC (ATCC #: CRL-5922; Manassas, Va. USA) and cultured in DMEM and RPMI without HEPES, respectively. The cells were trypsinized with 0.25% Trypsin-EDTA (Invitrogen, Grand Island, N.Y.). The doubling time of the H2087 cells was about 35 h. Cell lines were incubated at 37° C. in 5% $CO_2$ atmosphere.

Genistein (LC Laboratories, Woburn, Mass.) was dissolved in DMSO (Sigma, Oakville, Ontario) to prepare stock solutions of 2 and 20 mM and kept frozen at −20° C. until use. Decitabine (DAC, Dacogen™, 5-aza-2'-deoxycytidine) at 1000 µg/ml in PBS was kept at −80° C. Before each experiment, Decitabine was diluted at 1 µg/ml (for murine leukemic cell lines), 10 µg/ml (for human leukemic cells), or 100 µg/ml (for lung carcinoma cells) with sterile PBS and kept on ice until use.

Inhibition of clonogenicity. It is known that cancer cells form clones in soft agar (clonogenicity). Irreversible eradication of the clonogenicity of cancer stem cells is one of the objectives of chemotherapy since it is related to cell proliferation potential. Human and murine leukemic cell lines in log phase at $5 \times 10^4$ cells/ml were placed in tissue culture flasks and exposed to the drug combinations for 48 and 24 h respectively. Genistein was added at 0.1, 1 and 10 µM; Cells were concomitantly exposed to decitabine at 10 ng/ml (44 nM) for human leukemic cells, and 1 ng/ml (4.4 nM) for murine leukemic cells. Drugs were removed by centrifugation and cells were suspended in drug-free medium. Using a Beckman Z1™ Coulter Particle Counter (Hialeah, Fla.), 150 (for human leukemic cells) and 100 (for murine leukemic cells) cells were placed in 2 ml of 0.45% soft agar RPMI-1640 medium containing 20% (human cells) or 10% (murine cells) serum. After 7 d of incubation for murine cell lines or 15 d for human cell lines, the number of colonies (>50 cells) was counted. The cloning efficiency in soft agar in the absence of drug was in the range of 50-60% for all leukemic cell lines. The inhibition/loss of clonogenicity (%) was expressed relative to control cells (no drug treatment). All the experiments were performed in triplicate and the mean values were divided by the control mean value. The experiments were repeated three times and expressed as mean±S.E.M.

For human lung carcinoma H2087 cells, 100 cells were placed in wells of a 6-well dish (day 0); for Calu-6, MBA-MD-231 and Dld-1, 200 cells were seeded. On day 1, Decitabine (50 ng/ml) and genistein (5 µM) were added concomitantly to the cells for 24 h. Drugs were then removed and wells were rinsed with 1 ml of medium. Fresh medium (2 ml) was added and after 16-19 d colonies were stained with 0.5% methylene blue in 50% methanol and counted. The inhibition/loss of clonogenicity (%) was expressed relative to control (untreated) cells. The experiments were repeated three times and expressed as mean±S.D or mean±SEM for Calu-6, MBA-MD-231 and Dld-1 cells.

In vivo experiments. Male CD2F1 mice (24-28 g) were purchased from Taconic Biotechnology (Germantown, N.Y., USA). Mice were acclimatized to housing conditions at least 2 weeks before experiments. They received food and water ad libitum. For transplantation of leukemia cells in mice, intraperitonal (i.p.) injections of $10^4$ L1210 or L1210/ARAC cells in RPMI-1640 medium were performed weekly into the CD2F1 mice. Seven days later, the ascetic fluid was obtained from the mice and a cell count of the leukemic cells was performed with a haemocytometer prior to subsequent transplantation. Mice were injected intravenously (i.v.) with 0.1 ml of L1210 or L1210/ARAC ($10^4$) cells. Control groups that received the control diet 2016 (Teklad Global 16% Protein Rodent Diet™; Harlan Teklad, Madison Wis.) were either treated or not with DAC. To test the effect of genistein in the diet, mice were fed with 2016 diet supplemented with 0.5% genistein (Harlan Teklad) and treated with either DAC or the vehicle alone. Mice were acclimated to the genistein-enriched regimen over a 10-days period before injection of leukemic cells. A Harvard apparatus compact infusion pump was used at a flow rate of 0.22 ml/h via 25-gauge needle into the lateral tail vein. DAC was given at 2 mg/kg for 8 h. Decitabine was prepared fresh before each experiment, dissolved in ½ PBS and sterilized by 0.2 μm filtration. Mice were placed in a restrainer cage during treatment with access to food. Toxicity was evaluated by body weight loss. Mice fed with genistein-enriched diet kept the same regimen during all the experiment. The survival time of each group of mice was monitored and the increased in life span (ILS) calculated.

Statistical analyses. In order to evaluate whether the inter-group variations were random, one-way ANOVA testing was performed. The p value was evaluated accordingly to Tukey's method (Hastings, C et al. (1947). Ann. Math. Statist. 18,413-426). A p value≦0.05 was taken for statistical significance. Valeriote and Lin's method (Valeriote, F and Lin, H. S. 1975. Cancer Chemother. Rep. 59(5): 895-900) was used to determine if the interaction observed between drugs in the clonogenic assays was additive, synergistic or antagonistic.

Example 2

Figure 1B:
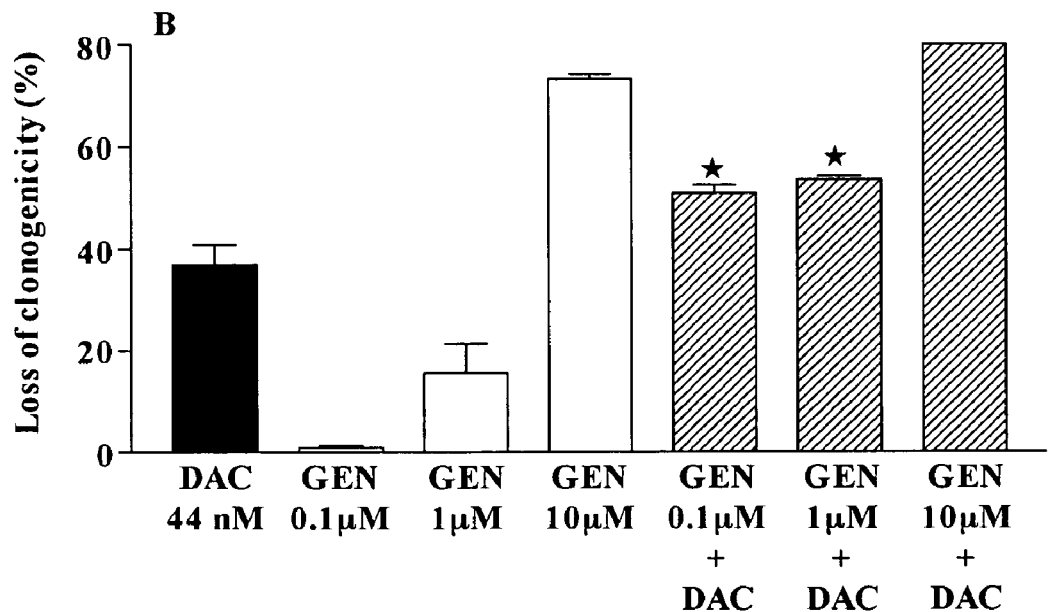

Effects of the Combination of Genistein and Decitabine on the Clonogenic Potential of Human Leukemic Cell Lines The effect of the combination of decitabine (DAC) and genistein on loss of clonogenicity was investigated for HL-60 myeloid (FIG. 1A) and MOLT-3 lymphoid (FIG. 1B) human leukemic cell lines. Both myeloid and lymphoid human leukemic cell lines showed a loss of clonogenicity after genistein exposure, where MOLT-3 cells were the most sensitive. DAC (44 nM) alone produced 20 and 40% loss of clonogenicity on HL-60 and MOLT-3 leukemic cells, respectively. For HL-60 cells (FIG. 1A), the combination of these two agents produced a synergistic activity on the loss of clonogenicity with the concentration of 0.1 and 1 μM of genistein. The loss of clonogenicity obtained for the combination (DAC+genistein 0.1 μM: 27% of loss of clonogenicity) was statistically significant (p<0.05) compared to DAC alone and was greater than the sum of the results obtained for genistein at 0.1 μM (1% of loss of clonogenicity) and for DAC (17% of loss of clonogenicity). The loss of clonogenicity obtained for the combination (DAC+genistein 1 μM: 43% of loss of clonogenicity) was statistically significant (p<0.01) compared to DAC alone and was greater than the sum of the results obtained for genistein at 1 μM (15% of loss of clonogenicity) and for DAC (17% of loss of clonogenicity).

For MOLT-3 cells (FIG. 1B), the combination of these two agents produced a synergistic activity on the loss of clonogenicity with the concentration of 0.1 and 1 μM of genistein. The loss of clonogenicity obtained for the combination (DAC+genistein 0.1 μM: 51% of loss of clonogenicity) was statistically significant (p<0.05) compared to DAC alone and was greater than the sum of the results obtained for genistein at 0.1 μM (1% of loss of clonogenicity) and for DAC (37% of loss of clonogenicity). The loss of clonogenicity obtained for the combination (DAC+genistein 1 μM: 53% of loss of clonogenicity) was statistically significant (p<0.05) compared to DAC alone and was greater than the sum of the results obtained for genistein at 1 μM (12% of loss of clonogenicity) and for DAC (37% of loss of clonogenicity).

Example 3

Figure 2A:
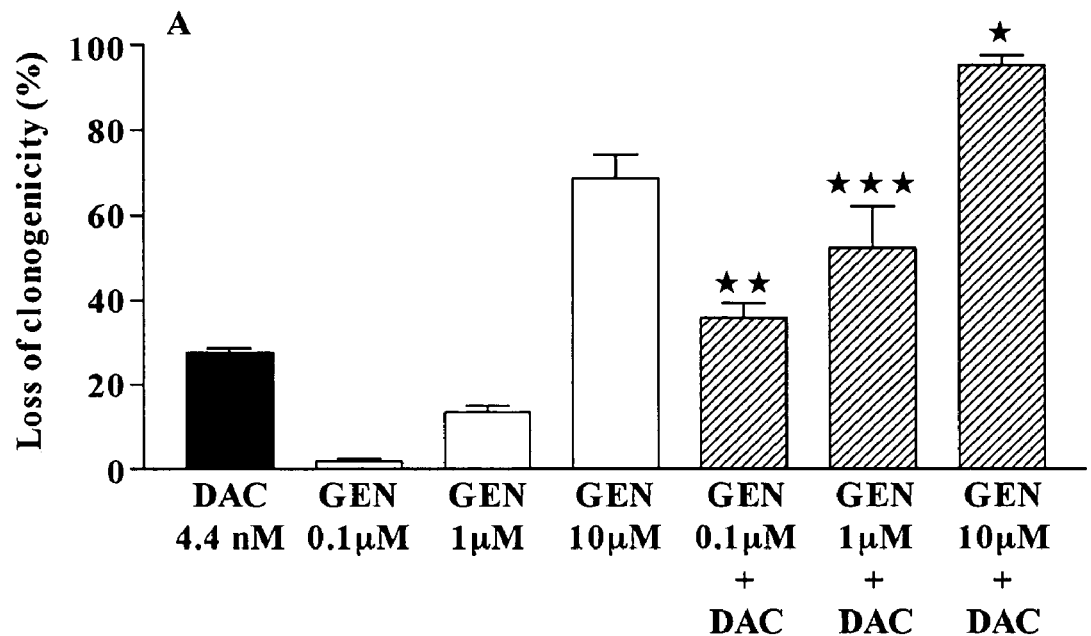
FIG. 2 shows the activation of decitabine (DAC) on loss of clonogenicity in murine leukemic cell lines. Results of loss of clonogenicity are expressed as mean±SEM compared to control cells (n=3). (A) L1210 murine lymphoid leukemic and (B) L1210/ARAC cell lines were exposed 48 h with DAC (4.4 nM) alone or in combination with different concentrations of genistein (0.1, 1 and 10 µM). *:p<0.05, :p<0.01, *: p<0.001.
Figure 2B:
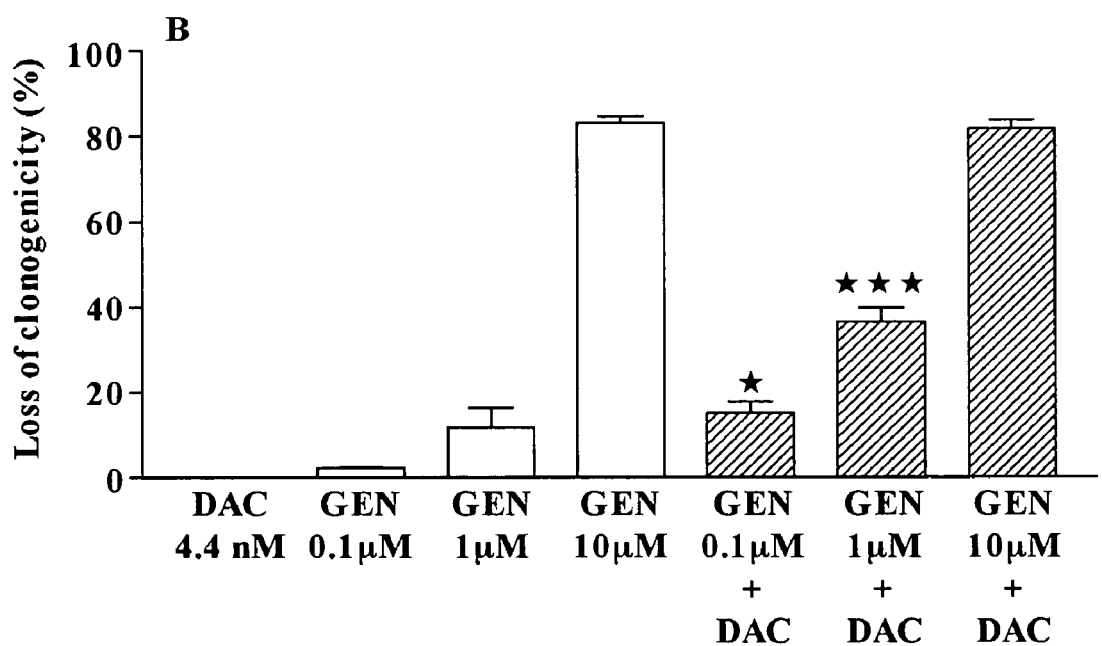

Effects of Combination of Genistein and Decitabine on the Clonogenic Potential of L1210 and L1210/ARAC Murine Leukemic Cell Lines The effect of the combination of decitabine (DAC) and genistein on loss of clonogenicity was investigated for lymphoid L1210 murine leukemic cells (FIG. 2A) and on their DAC-resistant clone L1210/ARAC (FIG. 2B). These cell lines showed a loss of clonogenicity after genistein exposure. Decitabine (4.4 nM) alone produced about 30% loss of clonogenicity on L1210 leukemic cells, whereas L1210/ARAC were not sensitive to DAC.

For L1210 cells (FIG. 2A), the combination of these two agents produced a synergistic activity on the loss of clonogenicity with genistein concentrations of 0.1 and 1 μM. The loss of clonogenicity obtained for the combination (DAC+genistein 0.1 μM: 36% of loss of clonogenicity) was statistically significant (p<0.01) compared to DAC alone and was greater than the sum of the results obtained for genistein at 0.1 μM (2% of loss of clonogenicity) and for DAC (28% of loss of clonogenicity). The loss of clonogenicity obtained for the combination (DAC+genistein 1 μM: 52% of loss of clonogenicity) was statistically significant (p<0.001) compared to DAC alone and was greater than the sum of the results obtained for genistein at 1 μM (13% of loss of clonogenicity) and for DAC (28% of loss of clonogenicity).

For L1210/ARAC cells (FIG. 2B), the combination of these two agents produced a potentiation of DAC activity on the loss of clonogenicity at genistein concentrations of 0.1 and 1 μM. The loss of clonogenicity obtained for the combination (DAC+genistein 0.1 μM: 23% of loss of clonogenicity) was statistically significant (p<0.05) compared to DAC alone and was greater than the sum of the results obtained for genistein at 0.1 μM (2% of loss of clonogenicity) and for DAC (0% of loss of clonogenicity). The loss of clonogenicity obtained for the combination (DAC+genistein 1 μM: 37% of loss of clonogenicity) was statistically significant (p<0.001) compared to DAC alone and was greater than the sum of the results obtained for genistein at 1 μM (11% of loss of clonogenicity) and for DAC (0% of loss of clonogenicity).

Example 4

Figure 6A:
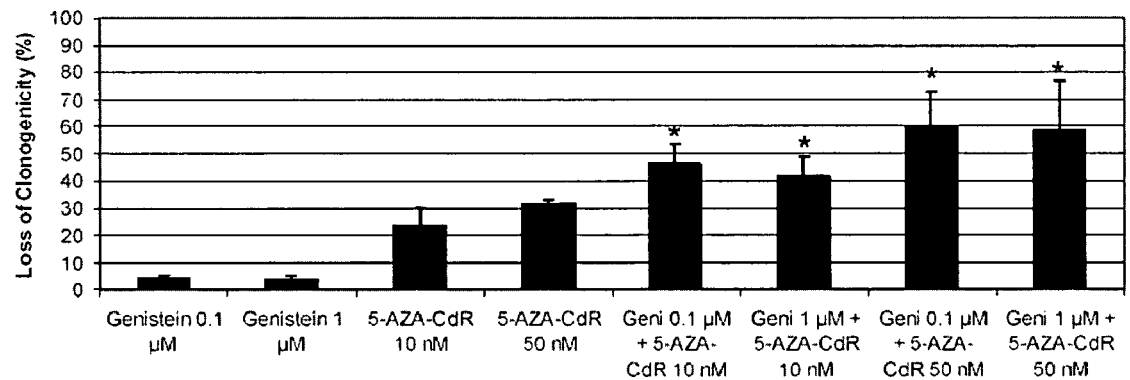
FIG. 6 shows the effect of a 48-hour exposure to 5-aza-2'-deoxycytidine (A: 10 or 50 nM; B: 50 nM) and/or genistein (0.1 or 1 µM) on the loss of clonogenicity of (A) Calu-6 tumor cells, and (B) MBA-MD-231 tumor cells (n=3). *=synergistic effect; 5-AZA-CdR=5-aza-2'-deoxycytidine.
Figure 6B:
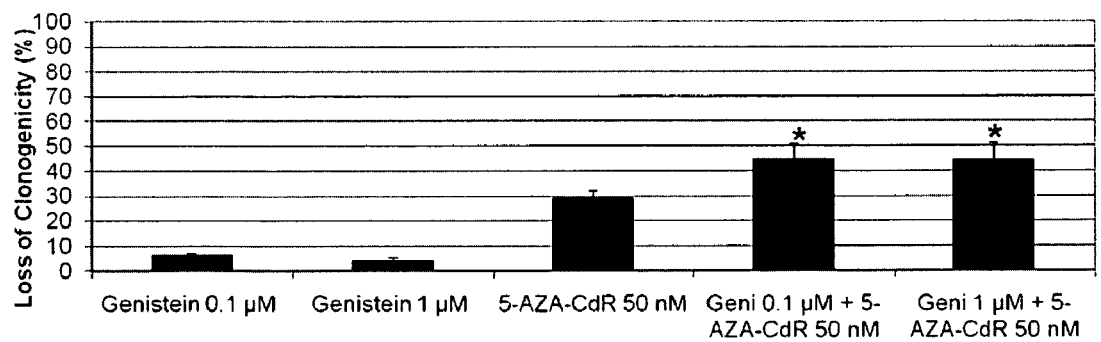
Figure 7:
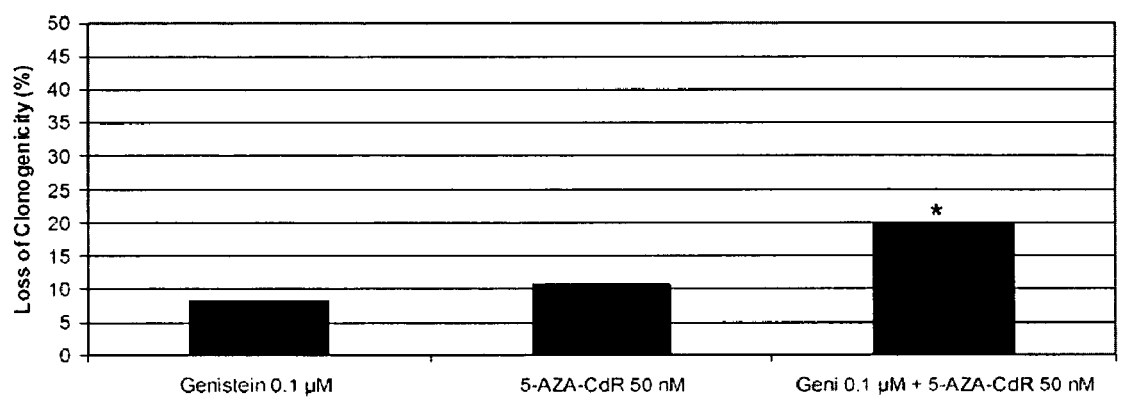
FIG. 7 shows the effect of a 48-hour exposure to 5-aza-2'-deoxycytidine (50 nM) and/or genistein (0.1 µM) on the loss of clonogenicity of Dld-1 tumor cells (n=1). *=synergistic effect; 5-AZA-CdR=5-aza-2'-deoxycytidine.

Effects of Combination of Genistein and Decitabine on the Clonogenic Potential of Various Tumor Cell Lines Results of the effect of the combination on lung H2087 adenocarcinoma cells are shown in Table I. The loss of clonogenicity obtained for the combination (DAC+genistein:

69% of loss of clonogenicity) was greater than the sum of the results obtained for genistein (3.8% of loss of clonogenicity) and for DAC (60% of loss of clonogenicity). Results of similar experiments performed using CALU-6 cells (human lung carcinoma cells) are shown in Table II and in FIG. 6A. For all concentrations of genistein tested (0.1, 1 and 10 μM), the loss of clonogenicity obtained for the combination was greater than the sum of the results obtained for genistein and for DAC. FIGS. 6B and 7 show the synergistic effect of genistein and 5-aza-2'-deoxycytidine on the loss of clonogenicity of MBA-MD-231 (breast) and Dld-1 (colon) tumor cells, respectively.

TABLE I

Effect of genistein on loss of clonogenicity in H2087 lung carcinoma cells.

| Treatment | Loss of clonogenicity (%) |
|---|---|
| Decitabine (220 nM) | 60 ± 4.1 |
| Genistein (5 μM) | 3.8 ± 9.4 |
| Decitabine (220 nM) + Genistein (5 μM) | 69.1 ± 3.6 |

Cells were treated with genistein at 5 μM for 24 h alone or in combination with 220 nM of decitabine (DAC). Colony formation assay were expressed in percentage relative to control (untreated) cells.
Data are mean values ± S.D.

TABLE II

Synergistic assessment of genistein and decitabine in a human lung carcinoma cell line (CALU-6).

| Treatment | Loss of clonogenicity (%) |
|---|---|
| Decitabine (10 ng/ml) | 36.6 |
| Genistein (0.1 μM) | 4.9 |
| Decitabine (10 ng/ml) + Genistein (0.1 μM) | 51.0 |
| Genistein (10 μM) | 31.7 |
| Decitabine (10 ng/ml) + Genistein (10 μM) | 81.7 |

Example 5

In vivo Effect of Genistein on L1210 Leukemic Mice

The potential chemotherapeutic activity of genistein against leukemia was tested in a mouse model. CD2F1 male mice were placed on 0.5% genistein-enriched diet (10-day period). The food intake was similar to the mice fed with control diet. The mice received i.v. injection of $10^4$ L1210 leukemic cells. Control mice survived 7.34±0.07 days after injection of leukemia. The leukemic mice fed with 0.5% genistein-enriched diet had a moderate, but significant, increase in survival and died at 7.85±0.10 (6.95%, $p<0.001$).

Example 6

In vivo Effect of a Genistein-enriched Diet Combined with DAC Chemotherapy in Mice Bearing L1210 or L1210/ARAC Leukemic Cells The antineoplastic activity of decitabine was tested in combination with genistein administered in the diet in a mouse model to evaluate the potential of this combination against leukemia. CD2F1 male mice were placed on 0.5% genistein-enriched diet (10-d period) or control diet. The food intake was similar to the mice fed with control diet. Note that the half-life of elimination of genistein in mice is much more rapid than in humans, and that blood levels after dietary intake are significantly lower in mice than in humans.

Figure 8:
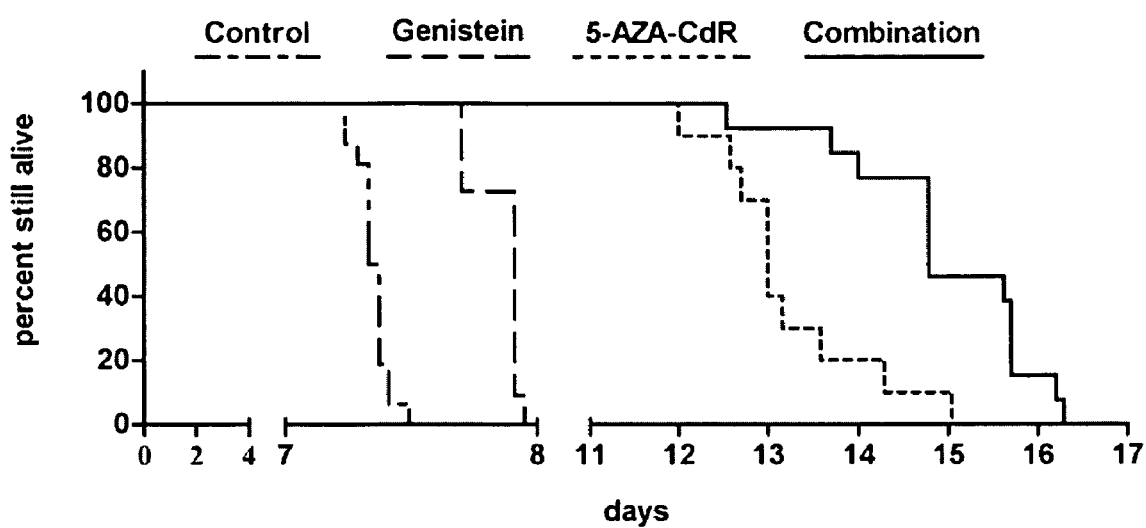
FIG. 8 shows the effect of a 8 h i.v. infusion of 5-AZA-CdR (2 mg/kg total dose) and/or a 0.5% genistein-enriched diet on the survival time of CD2F1 mice bearing L1210 leukemia. The survival time (h) of control (n=11), genistein (n=11), 5-AZA-CdR (n=10) and genistein plus 5-AZA-CdR-treated mice (n=13), is shown on a Kaplan-Meier survival curve. The mice received i.v. injection of leukemia on day 0.

First, the effect of this combination was tested against mice bearing L1210 leukemic cells (Table III). As shown in Example 5, leukemic mice fed with a genistein-enriched diet had a moderate but significant increase in life span of 7.0% ($p<0.001$). Chemotherapy of DAC produced an increase in life span of 66.8% (Table III). Mice treated with the combination had a synergistic increase in life span of 86.7% ($p<0.01$) compared to the mice treated with DAC alone. FIG. 8 shows the Kaplan-Meier survival curves for all the treated animals.

TABLE III

Effect of a 0.5% genistein-enriched diet on survival time of DAC-treated CD2F1 mice bearing L1210 leukemic cells.

| Mice bearing L1210 leukemia | Increase in life span (%) |
|---|---|
| Control (n = 10) | — |
| 0.5% of genistein in the diet (n = 10) | 7.0. ($p < 0.001$) |
| DAC at 2 mg/kg for 8 hours (n = 10) | 66.8 |
| DAC on mice fed with 0.5% of genistein in the diet (n = 13) | 86.7 ($p < 0.01$) |

Mice that were acclimated to the genistein-enriched diet prior to the start of treatments and stayed on this typical diet during all the experiment. Mice received an i.v. injection of $10^4$ L1210 leukemic cells on day 0 and were infused with DAC (8 hours at 2 mg/kg) or vehicle alone on day 1. Survival time was determined, and the increase in life span produced by the combination of genistein-enriched diet with DAC was calculated. Statistical analysis were made using ANOVA followed by the Tukey-Kramer Multiple Comparisons Test.

The effect of this combination was then investigated against mice bearing L1210/ARAC leukemic cells (Table IV). This cell line is totally resistant to DAC and the mechanism of resistance is the same of what in observed in resistant-patients to DAC. Leukemic mice fed with 0.5% genistein-enriched diet had a non-significant increase in life span (7.88%) compared to controls. Administration of DAC failed to increase the life span of mice bearing L1210/ARAC leukemic cells resistant to DAC. Mice bearing DAC-resistant cells that followed DAC-chemotherapy and fed with 0.5% genistein-enriched diet showed a significant increase of 11.36% in life span ($p<0.05$) compare to DAC alone. The relative increase in life span obtained for the combination (11.36%) was greater than the sum of the results obtained for genistein (7.88%) and for DAC (−2.3%).

TABLE IV

Effect of a 0.5% genistein-enriched diet on survival time of DAC-treated CD2F1 mice bearing L1210/ARAC leukemic cells.

| Mice bearing L1210/ARAC leukemia | Survival time (days) | Increase in life span (%) |
|---|---|---|
| Control (n = 10) | 9.64 ± 0.44 | — |
| 0.5% of genistein in the diet (n = 10) | 10.39 ± 1.01 | 7.88 |
| DAC at 2 mg/kg for 8 hours (n = 10) | 9.42 ± 0.50 | −2.3 |
| DAC on mice fed with 0.5% of genistein in the diet (n = 10) | 10.49 ± 1.11 ($p < 0.05$) | 11.36 |

Mice that were acclimated to the genistein-enriched diet during all the experiment. Mice received an i.v. injection of $10^4$ L1210/ARAC leukemic cells on day 0 and were infused with DAC (8 hours at 2 mg/kg) or vehicle alone on day 1. Survival time was determined, and the increase in life span produced by the combination of genistein-enriched diet with DAC was calculated. Statistical analysis were made using ANOVA followed by the Tukey-Kramer Multiple Comparisons Test.

Example 7

Figure 3A:
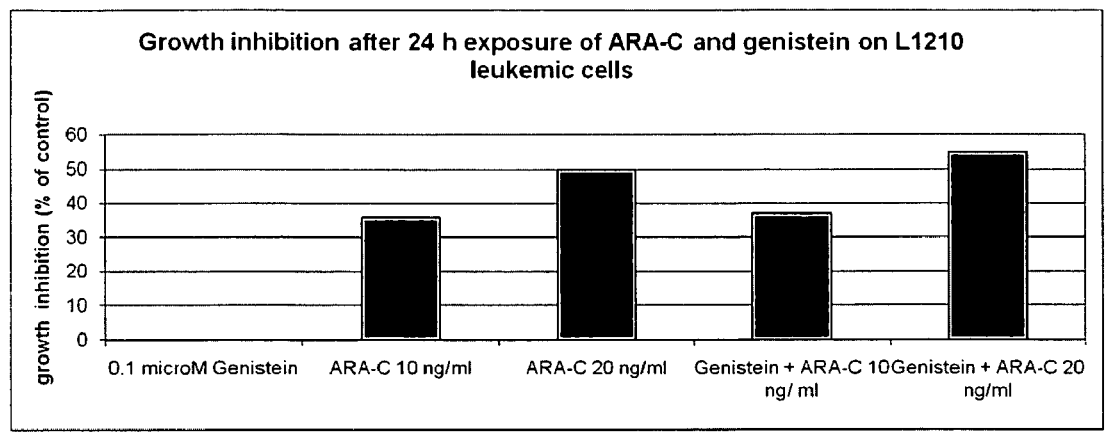
FIG. 3 shows the effect of a 24-hour exposure to cytarabine (ARA-C) and/or genistein (0.1 µM) on the growth inhibition and (A) the loss of clonogenicity (B) of L1210 leukemic cells.
Figure 3B:
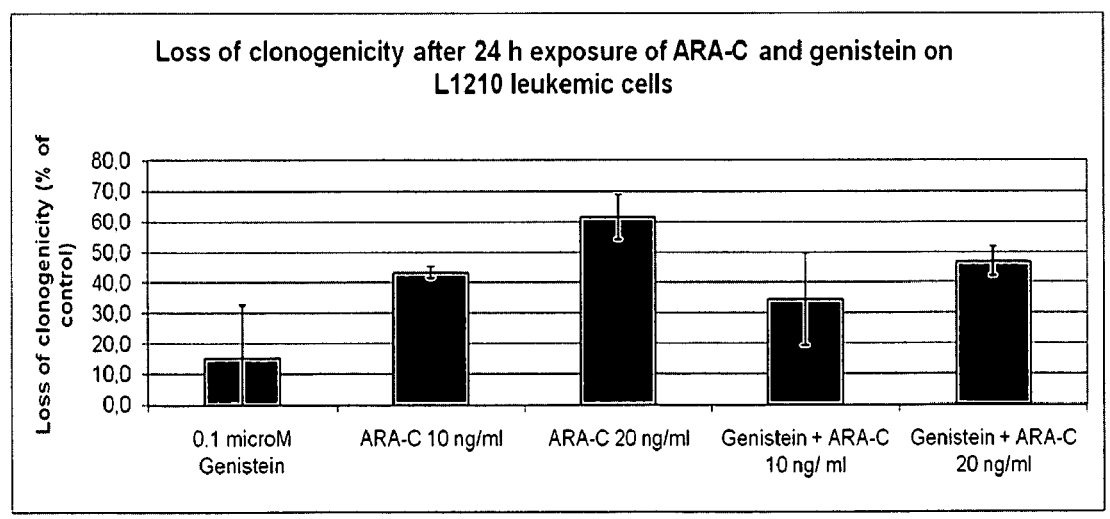
Figure 4A:
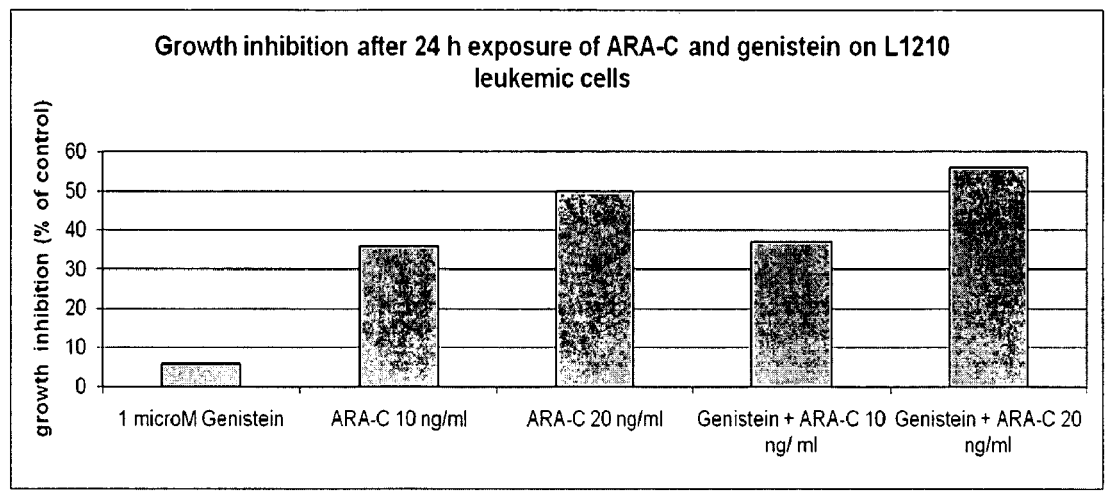
FIG. 4 shows the effect of a 24-hour exposure to cytarabine (ARA-C) and/or genistein (1 µM) on the growth inhibition and (A) the loss of clonogenicity (B) of L1210 leukemic cells.
Figure 4B:
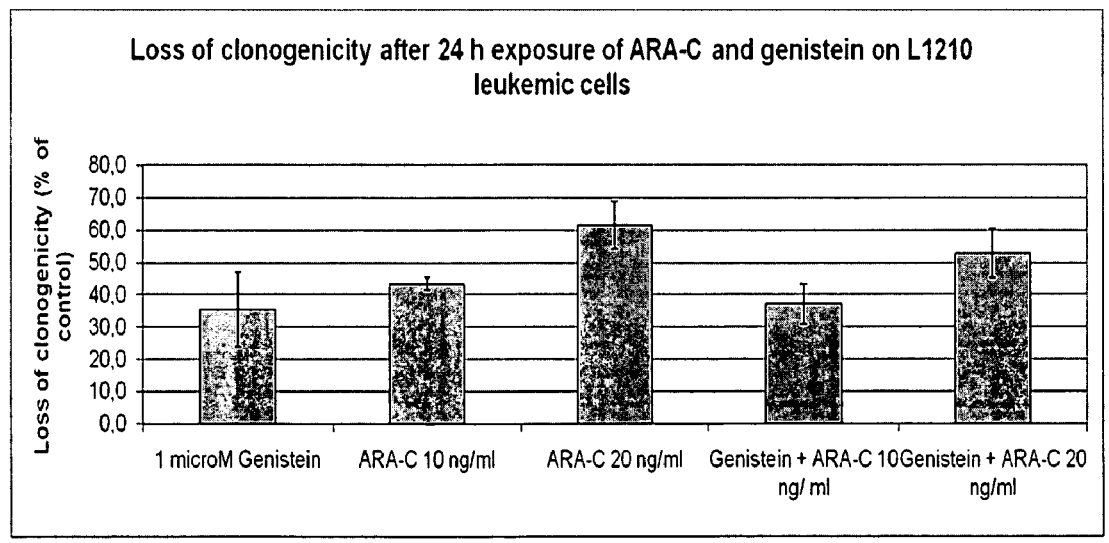

Effect of Cytarabine (ARA-C) and/or Genistein on the Growth Inhibition and Loss of Clonogenicity of L1210 Leukemic Cells FIG. 3 shows the effect of a 24-hour exposure to cytarabine (10 and 20 ng/ml) and/or genistein (0.1 µM) on the growth (FIG. 3A) and loss of clonogenicity (FIG. 3B) of L1210 leukemic cells. FIG. 4 shows the effect of a 24-hour exposure to cytarabine (10 and 20 ng/ml) and/or genistein (1 µM) on the growth (FIG. 4A) and loss of clonogenicity (FIG. 4B) of L1210 leukemic cells.

Example 8

Figure 5:
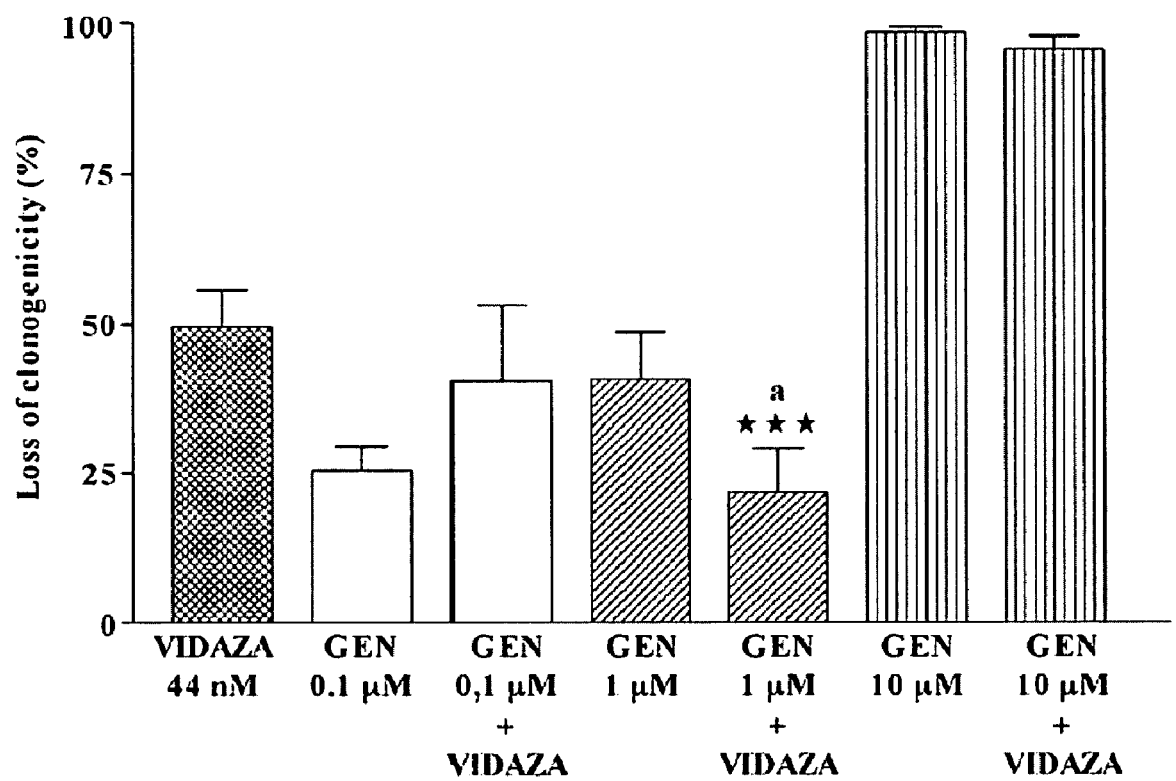
FIG. 5 shows the effect of a 48-hour exposure to 5-aza-cytidine (Vidaza™; 44 µM) and/or genistein (0.1, 1 or 10 µM) on the loss of clonogenicity of L1210 leukemic cells.

Effect of 5-aza-cytidine (Vidaza™) and/or Genistein on the Loss of Clonogenicity of L1210 Leukemic Cells FIG. 5 shows the effect of a 48-hour exposure to 5-aza-cytidine (44 nM) and/or genistein (0.1, 1 and 10 µM) on the loss of clonogenicity of L1210 leukemic cells.

Although the present invention has been described hereinabove by way of specific embodiments thereof, it can be modified, without departing from the spirit and nature of the subject invention as defined in the appended claims.

The invention claimed is:

1. A method of treating cancer in a subject in need thereof, said method comprising administering (i) 5-aza-2'-deoxycytidine and (ii) genistein to said subject, wherein said cancer is leukemia, lung cancer, colon cancer or breast cancer.

2. The method of claim 1, wherein said cancer is leukemia.

3. The method of claim 1, wherein said cancer is lung cancer.

4. The method of claim 1, wherein said cancer is colon cancer.

5. The method of claim 1, wherein said cancer is breast cancer.

6. The method of claim 1, wherein said subject is a mammal.

7. The method of claim 6, wherein said mammal is a human.

8. The method of claim 1, wherein said 5-aza-2'-deoxycytidine and said genistein are administered simultaneously.

9. The method of claim 1, wherein said 5-aza-2'-deoxycytidine and said genistein are administered sequentially.

10. The method of claim 1, wherein said method comprises administering a pharmaceutical composition comprising said 5-aza-2'-deoxycytidine, said genistein and a pharmaceutically acceptable carrier.

* * * * *